United States Patent
Van Andel

(10) Patent No.: US 8,063,271 B2
(45) Date of Patent: Nov. 22, 2011

(54) **INBRED RADISH LINE *NIZ-AC2***

(75) Inventor: Andre Van Andel, Tuitjenhorn (NL)

(73) Assignee: Nickerson-Zwaan B.V., PM Made (NL)

( * ) Notice: Subject to any disclaimer, the term of this patent is extended or adjusted under 35 U.S.C. 154(b) by 273 days.

(21) Appl. No.: 12/497,313

(22) Filed: Jul. 2, 2009

(65) Prior Publication Data

US 2009/0307792 A1    Dec. 10, 2009

(51) Int. Cl.
*A01H 5/00* (2006.01)
*A01H 1/00* (2006.01)
*A01H 5/10* (2006.01)

(52) U.S. Cl. .................... 800/306; 800/260; 435/410
(58) Field of Classification Search .................. None
See application file for complete search history.

(56) References Cited

U.S. PATENT DOCUMENTS

| | | |
|---|---|---|
| 5,304,719 A | 4/1994 | Segebart |
| 5,367,109 A | 11/1994 | Segebart |
| 5,523,520 A | 6/1996 | Hunsperger et al. |
| 5,763,755 A | 6/1998 | Carlone |
| 5,850,009 A | 12/1998 | Kevern |

OTHER PUBLICATIONS

US PVP Application No. 8300024 for radish cultivar Red King, USDA Dec. 30, 1983.*
Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. App. Genet. 101:323-326.
Poehlman, J.M. and Sleper, D.A., Methods in Plant Breeding, in Breeding Field Crops, 4th ed. (1995), Iowa State University Press, pp. 172-174.
Narvel, et al., 2001. A Retrospective DNA Marker Assessment of the Development of Insect Resistant Soybean. Crop Sci. 41:1931-1939.
Goldman, et al., 1994. Molecular Markers Associated with Maize Kernel Oil Concentration in an Illinois High Protein x Illinois Low Protein Cross. Crop Sci. 34: 908-915.

* cited by examiner

*Primary Examiner* — Elizabeth McElwain
(74) *Attorney, Agent, or Firm* — Jondle & Associates, P.C.

(57) ABSTRACT

An inbred radish line having resistance to white rust (*Albugo candida*), designated NIZ-AC2, is disclosed. The invention relates to the seeds of inbred radish line NIZ-AC2, to the plants and plant parts of inbred radish line NIZ-AC2 and to methods for producing a radish plant, either inbred or hybrid, by crossing the inbred line NIZ-AC2 with itself or another radish line. The invention further relates to methods for producing a radish plant containing in its genetic material one or more transgenes and to the transgenic plants produced by that method and to methods for producing other inbred radish lines derived from the inbred NIZ-AC2.

19 Claims, No Drawings

INBRED RADISH LINE NIZ-AC2

BACKGROUND OF THE INVENTION

The present invention relates to a new and distinctive radish cultivar, designated NIZ-AC2 (*Raphanus sativus* sp.). The present invention further relates to round red hybrid radish resistant to white blister caused by *Albugo candida*. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, rounder shape, smoother texture, root size, higher seed yield, improved color, resistance to diseases and insects, tolerance to drought and heat, as well as better agronomic quality. With mechanical harvesting of many crops, uniformity of plant characteristics such as germination and stand establishment, growth rate, maturity is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of breeding method. Backcross breeding is used to transfer one or a few favorable genes for a heritable trait into a desirable cultivar. This approach has been used extensively for breeding disease-resistant cultivars; nevertheless, it is also suitable for the adjustment and selection of morphological characters, color characteristics and simply inherited quantitative characters such as earliness, plant height or seed size and shape. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three or more years. The best lines are candidates for use as parents in new commercial cultivars; those still deficient in a few traits may be used as parents to produce new populations for further selection.

These processes, which lead to the final step of marketing and distribution, usually take from ten to twenty years from the time the first cross is made. Therefore, development of new cultivars is a time-consuming process that requires precise forward planning, efficient use of resources, and a focus on clear objectives.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of radish breeding is to develop new, unique and superior radish lines and hybrids. The breeder initially selects and crosses two or more parental lines, followed by repeated self pollination or selfing and selection, producing many new genetic combinations. Another method used to develop new, unique and superior radish inbred lines and hybrids occurs when the breeder selects and crosses two or more parental lines, followed by haploid induction and chromosome doubling that results in the development of dihaploid inbred lines. The breeder can theoretically generate billions of different genetic combinations via crossing, selfing and mutations and the same is true for the utilization of the dihaploid breeding method. The breeder has no direct control at the cellular level. Therefore, two breeders will never develop the same line, or even very similar lines, having the same radish traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures or dihaploid breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the same original parents and the same selection techniques. This unpredictability results in the expenditure of large research funds to develop a superior new radish inbred line.

The development of commercial radish hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes or through the dihaploid breeding method followed by the selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars. Similarly, the development of new inbred lines through the dihaploid system requires the selection of the best inbreds followed by four to five years of testing in hybrid combinations in replicated plots.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population, will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into radish varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

Descriptions of other breeding methods that are commonly used for different traits and crops can be found in one of several reference books (e.g., Allard, *Principles of Plant Breeding*, John Wiley and Son, pp. 115-161 (1960), Fehr (1987)).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock. In some cases for example, where the production of the $F_1$ seeds is low, three way hybrids can be generated. Three way hybrids are created by crossing two inbred lines (A×B) to make a hybrid parent which is itself crossed with another inbred line ((A×B)×C) to generate the three way hybrid.

Hybrid radish seed is typically produced by a male sterility system such as the cytoplasmic male-sterile (CMS) system. Plants of a CMS inbred are male sterile as a result of factors resulting from the cytoplasmic, as opposed to the nuclear, genome. Thus, this characteristic is inherited exclusively through the female parent in radish plants, since only the female provides cytoplasm to the fertilized seed.

Radish is an important and valuable vegetable crop. Thus, a continuing goal of radish plant breeders is to develop stable, high yielding radish hybrids that are agronomically sound. To accomplish this goal, the radish breeder must select and develop radish plants that have the traits that result in superior parental lines for producing hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided an inbred radish line, designated NIZ-AC2. This invention thus relates to the seeds of inbred radish line NIZ-AC2, to the plants or parts thereof of inbred radish line NIZ-AC2, to plants or parts thereof having all the physiological and morphological characteristics of inbred radish line NIZ-AC2 and to plants or parts thereof having all the physiological and morphological characteristics of inbred radish line NIZ-AC2 listed in Table 1. Parts of the inbred radish plant of the present invention are also provided, such as e.g., pollen obtained from an inbred plant and an ovule of the inbred plant.

In another aspect, the present invention provides regenerable cells for use in tissue culture of inbred radish plant NIZ-AC2. The tissue culture will preferably be capable of regenerating plants having all the physiological and morphological characteristics of the foregoing inbred radish plant. Preferably, the cells of such tissue cultures will be embryos, ovules, meristematic cells, seeds, callus, pollen, leaves, anthers, pistils, roots, root tips, flowers, hypocotyl, or the like. Protoplasts produced from such tissue culture are also included in the present invention. The radish plants regenerated from the tissue cultures are also part of the invention.

Also included in this invention are methods for producing a radish plant produced by crossing the inbred line NIZ-AC2 with itself or another radish that can be another radish line or a radish hybrid in three-way hybrid production. When crossed with itself, i.e. crossed with another inbred line NIZ-AC2 plant or self-pollinated, the inbred line NIZ-AC2 will be conserved. When crossed with another, different radish line, an $F_1$ hybrid seed is produced. $F_1$ hybrid seeds and plants produced by growing said hybrid seeds are included in the present invention. A method for producing an $F_1$ hybrid radish seed comprising crossing inbred line NIZ-AC2 radish plant with a different radish plant and harvesting the resultant hybrid radish seed are also part of the invention. The hybrid radish seed produced by the method comprising crossing inbred line NIZ-AC2 radish plant with a different radish plant and harvesting the resultant hybrid radish seed are included in the invention, as are included the hybrid radish plant or parts thereof, seeds included, produced by growing said hybrid radish seed.

When crossed with another, different radish hybrid, an $F_1$ three-way hybrid seed is produced. Such $F_1$ three-way hybrid seeds and plants produced by growing said three-way hybrid seeds are included in the present invention. A method for producing an $F_1$ three-way hybrid radish seed comprising crossing inbred line NIZ-AC2 radish plant with a different hybrid radish plant and harvesting the resultant three-way hybrid radish seed are also part of the invention. The three-way hybrid radish seed produced by the method comprising crossing inbred line NIZ-AC2 radish plant with a different hybrid radish plant and harvesting the resultant three-way hybrid radish seed are included in the invention, as are included the three-way hybrid radish plant or parts thereof, seeds included, produced by growing said three-way hybrid radish seed.

In another embodiment, this invention relates to a method for producing the inbred line NIZ-AC2 from a collection of seeds, the collection containing both inbred line NIZ-AC2 seeds and hybrid seeds having NIZ-AC2 as a parental line. Such a collection of seed might be a commercial bag of seeds. Said method comprises planting the collection of seeds. When planted, the collection of seeds will produce inbred line NIZ-AC2 plants from inbred line NIZ-AC2 seeds and hybrid plants from hybrid seeds. The plants having all the physiological and morphological characteristics of radish inbred line NIZ-AC2 or having a decreased vigor compared to the other plants grown from the collection of seeds are identified as inbred line NIZ-AC2 parent plants. Said decreased vigor is due to the inbreeding depression effect and can be identified for example by a less vigorous appearance for vegetative and/or reproductive characteristics including shorter plant height, smaller root or other characteristics. As previously mentioned, if the inbred line NIZ-AC2 is self-pollinated, the inbred line NIZ-AC2 will be preserved, therefore, the next step is controlling pollination of the inbred parent plants in a manner which preserves the homozygosity of said inbred line NIZ-AC2 parent plant, and the final step is to harvest the resultant seed.

This invention also relates to methods for producing other inbred radish lines derived from inbred radish line NIZ-AC2 and to the inbred radish lines derived by the use of those methods.

In another aspect, the present invention provides for methods of introducing one or more desired trait(s) into the radish line NIZ-AC2 and plants or seeds obtained from such methods. The desired trait(s) may be, but not exclusively, a single gene, preferably a dominant but also a recessive allele. Preferably, the transferred gene or genes will confer such traits as male sterility, herbicide resistance, insect resistance, disease resistance, resistance for bacterial, fungal, or viral disease, male fertility, water stress tolerance, enhanced nutritional quality, modified protein content, enhanced plant quality, enhanced digestibility and industrial usage. The gene or genes may be naturally occurring radish gene(s). The method for introducing the desired trait(s) is preferably a backcrossing process making use of a series of backcrosses to the inbred radish line NIZ-AC2 during which the desired trait(s) is maintained by selection.

The backcross breeding process comprises the following steps: (a) crossing the inbred line NIZ-AC2 plants with plants of another line that comprise the desired trait(s), (b) selecting the $F_1$ progeny plants that have the desired trait(s); (c) crossing the selected $F_1$ progeny plants with the inbred line NIZ-AC2 plants to produce backcross progeny plants; (d) selecting for backcross progeny plants that have the desired trait(s) and physiological and morphological characteristics of radish inbred line NIZ-AC2 to produce selected backcross progeny plants; and (e) repeating steps (c) and (d) one, two, three, four, five, six, seven, eight, nine or more times in succession to produce selected, second, third, fourth, fifth, sixth, seventh, eighth, ninth or higher backcross progeny plants that comprise the desired trait(s) and all the physiological and morphological characteristics of radish inbred line NIZ-AC2 as listed in Table 1. The radish plants or seeds produced by the methods are also part of the invention. Backcrossing breeding methods, well known to one skilled in the art of plant breeding will be further developed in subsequent parts of the specification.

In an embodiment of this invention is a method of making a backcross conversion of radish inbred line NIZ-AC2, comprising the steps of crossing a plant of radish inbred line NIZ-AC2 with a donor plant comprising a gene conferring a desired trait, selecting an $F_1$ progeny plant comprising the gene conferring the desired trait, and backcrossing the selected $F_1$ progeny plant to a plant of radish inbred line NIZ-AC2. This method may further comprise the step of obtaining a molecular marker profile of radish inbred line NIZ-AC2 and using the molecular marker profile to select for a progeny plant with the desired trait and the molecular marker profile of NIZ-AC2. In the same manner, this method may be used to produce an $F_1$ hybrid seed by adding a final step of crossing the desired trait conversion of radish inbred line NIZ-AC2 with a different radish plant to make F1 hybrid radish seed comprising a gene conferring the desired trait. The different radish plant may be an inbred or a hybrid plant.

In a preferred embodiment, the present invention provides methods for increasing and producing inbred line NIZ-AC2 seed, whether by crossing a first inbred parent radish plant with a second inbred parent radish plant and harvesting the resultant radish seed, wherein both said first and second inbred radish plant are the inbred line NIZ-AC2 or by planting an inbred radish seed of the inbred radish line NIZ-AC2, growing an inbred line NIZ-AC2 plant from said seed, controlling a self pollination of the plant where the pollen produced by the grown inbred line NIZ-AC2 plant pollinates the ovules produced by the very same inbred line NIZ-AC2 grown plant and harvesting the resultant seed.

The invention further provides methods for developing radish plants in a radish plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, etc.) enhanced selection, genetic marker enhanced selection and transformation. Radish seeds, plants, and parts thereof produced by such breeding methods are also part of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Collection of seeds. In the context of the present invention a collection of seeds will be a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Decreased vigor. A plant having a decreased vigor in the present invention is a plant that, compared to other plants has a less vigorous appearance for vegetative and/or reproductive characteristics including shorter plant height, color or other characteristics.

Disease. Disease, as used herein, is understood to be fungal disease, viral disease, bacterial disease or other plant pathogenic disease. Disease resistant plant encompasses plants resistant to fungal, viral, bacterial and other plant pathogens.

Disease Resistance. As used herein, the term "disease resistance" is defined as the ability of plants to restrict the activities, growth and development of a specified pest or pathogen such as an insect, fungus, virus, or bacterium and/or the damage they cause when compared to susceptible plant varieties under similar environmental conditions and pest or pathogen pressure. Resistant varieties may exhibit some disease symptoms or damage under heavy pest or pathogen pressure. Two levels of resistance are defined: High/standard resistance (HR): plant varieties that highly restrict the growth and development of the specified pest or pathogen under normal pest or pathogen pressure when compared to susceptible varieties. These plant varieties may, however, exhibit some symptoms or damage under heavy pest or pathogen pressure. Moderate/intermediate resistance (IR): plant varieties that restrict the growth and development of the specified pest or pathogen, but may exhibit a greater range of symptoms or damage compared to high/standard resistant varieties.

Disease Tolerance. As used herein, the term "disease tolerance" is defined as the ability of plants to endure a specified pest (such as an insect, fungus, virus or bacterium) or an adverse environmental condition and still perform and produce in spite of this disorder.

Essentially all of the physiological and morphological characteristics. A plant having essentially all of the physiological and morphological characteristics means a plant having the physiological and morphological characteristics of the recurrent parent, except for the characteristics derived from the converted gene.

Gene. As used herein, "gene" refers to a segment of nucleic acid. A gene can be introduced into a genome of a species, whether from a different species or from the same species, using transformation or various breeding methods.

Gene converted. Gene converted or conversion plants refers to plants which are developed by a plant breeding technique called backcrossing wherein essentially all the morphological and physiological characteristics of an inbred are recovered in addition to the one or more genes transferred into the inbred via the backcrossing technique, via genetic engineering or mutation. This also includes transference of one or more loci.

Inbreeding depression. The inbreeding depression is the loss of performance of the inbreds due to the effect of inbreeding, i.e. due to the mating of relatives or to self-pollination. It increases the homozygous recessive alleles leading to plants which are weaker and smaller and having other less desirable traits.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Pedigree Distance. Relationship among generations based on their ancestral links as evidenced in pedigrees. May be measured by the distance of the pedigree from a given starting point in the ancestry.

Percent Identity. Percent identity as used herein refers to the comparison of the homozygous alleles of two radish varieties. Percent identity is determined by comparing a statistically significant number of the homozygous alleles of two developed varieties. For example, a percent identity of 90% between radish variety 1 and radish variety 2 means that the two varieties have the same allele at 90% of their loci.

Percent Similarity. Percent similarity as used herein refers to the comparison of the homozygous alleles of a radish variety such as NIZ-AC2 with the alleles of another radish plant, and if the homozygous alleles of NIZ-AC2 matches at least one of the alleles from the other plant then they are scored as similar. Percent similarity is determined by comparing a statistically significant number of loci and recording the number of loci with similar alleles as a percentage. A percent similarity of 90% between NIZ-AC2 and another radish plant means that NIZ-AC2 matches at least one of the alleles of the other plant at 90% of the loci.

Plant cell. Plant cell, as used herein includes plant cells whether isolated, in tissue culture, or incorporated in a plant or plant part.

Plant height. This is a measure of the height of the plant, whether inbred or hybrid, from the ground to the top of the uppermost leaf, and is measured in centimeters.

Plant part. As used herein, the term "plant parts" (or a radish plant, or a part thereof) includes but is not limited to protoplasts, callus, leaves, stems, roots, root tips, anthers, pistils, seed, embryos, pollen, ovules, cotyledon, hypocotyl, flower, shoot, tissue, petiole, cells, meristematic cells and the like.

Progeny. As used herein, progeny includes an $F_1$ radish plant produced from the cross of two radish plants where at least one plant includes radish cultivar NIZ-AC2. Progeny further includes but is not limited to subsequent $F_2, F_3, F_4, F_5, F_6, F_7, F_8, F_9$ and $F_{10}$ generational crosses with the recurrent parental line.

Quantitative trait loci (QTL) Quantitative trait loci refer to genetic loci that control to some degree numerically representable traits that are usually continuously distributed.

Regeneration. Regeneration refers to the development of a plant from tissue culture.

Susceptibility. As used herein, the term "Susceptibility" is the inability of a plant variety to restrict the growth and development of a specified pest or pathogen.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International Convention for the Protection of New Varieties of Plants)

DETAILED DESCRIPTION OF THE INVENTION

All cultivated forms of radish belong to the family Cruciferae (alt. Brassicaceae), and are grown for their edible hypocotyl. Radishes have been cultivated for thousands of years in both China and the Mediterranean areas. Generally, commercial radishes are grown wherever environmental conditions permit the production of an economically viable yield. The radish grown in the United States is primarily an annual, although biennial types occur. In the United States, the top producing states for radish (*Raphanus sativus*) are Florida (32 percent), California (20 percent), Michigan (16 percent), Minnesota (10 percent), and Ohio (7 percent). Fresh radish is available in the United States year-round, where domestic supplies are the highest from May to October, while imports are at their peak from November to April. For planting purposes, radishes grow best in rather cool weather—fall and spring of the Northern states and late fall, winter, and early spring in the warmer states. Radish is consumed mainly as a salad plant and eaten raw, but can be eaten as a cooked or pickled vegetable.

Radish is a quick growing, primarily annual, cool season root vegetable that matures in 3 to 6 weeks. The seed will germinate in 3 to 4 days with soil temperatures of 18° C. to 30° C., but germination rates decline sharply when the soil temperatures fall below 13 degrees C. The best quality and root shape are obtained when the crop grows and matures at moderate temperatures of 10° C. to 30° C. in intermediate to short day lengths. When grown in hot weather, radishes tend to elongate, develop poor shape or no edible hypocotyl at all, and become more pungent. When grown in cold weather, radish tops grow larger and taller, while long days induce flowering or bolting. Thus, growth must be continuous and rapid for good quality. Radishes remain in prime condition only for a few days, as the edible hypocotyl remains in marketable condition only a short time before becoming pithy.

The radish (*Raphanus sativus*) is an extremely variable vegetable. Some radishes are annuals, little more than 4 inches (10 cm) tall at maturity, and some are biennials, going to seed in their second growing season, and topping out at over 6 ft (1.8 m) in height. Most radish types are grown for their enlarged roots, and there is great variation in size, shape and color. Some are small "salad radishes" with red skins or pure white throughout. These are mostly cool-season annuals, harvested young and usually eaten raw. Other radishes get huge, up to 60 lb (27 kg). Most of these "daikon" types are biennials, harvested after a longer growing season, and cooked before eating. Some radish cultivars are grown just for the seed pods which are delicious raw, pickled or in stir fry.

These are called bier radishes in Germany (and served raw with beer), and rat-tailed radishes in the Far East. Some radish cultivars are grown for the high quality oil that is extracted from the seeds. There are even cultivars grown for the leaves, which are cooked as potherbs, and some grown for sprouting.

The colors of the outer skin can vary widely among the various radishes from red, pink, purple, white, white with green shoulders, green, yellow, red with a white tip up to black skins. The flesh can vary also with most having white flesh, but some having pink or red flesh. The shape can also vary from round, round elongated, rat-tailed and long types.

When looking at the size, the radishes can be small-sized globe or round radishes with a size from 1 to 1.5 inches up to 4 to 5 inches, small long types with roots up to 4 inches, small rat-tailed roots up to 5 inches and the big long-sized "Daikon" types which can grow up to 18 inches.

The round red radishes can be distinguished from the other radish types by the round or round elongated shape, the red color of the skin and the size of the radish (1 to 1.5 inches up to 4 to 5 inches). Round red radishes with their leaves intact are usually tied in bunches, while topped radishes are sold in plastic bags. If the leaves are attached, they should be crisp and green. The roots should be hard and solid, with a smooth, unblemished surface.

Radish is subject to different pathogen and disease attacks such as white rust caused by the oomycete *Albugo candida* (Pers. ex. Lev.) Kuntze which is an obligate biotrophic pathogen of crucifers (Brassicaceae). White rust (also known as white blister or staghead, caused by *A. cruciferum* or *A. cruciferatum*) is destructive to many vegetable crops and oilseed crops such as cabbage, rape, mustard and radish. The fungus is highly specialized, grows between living host cells and causes a range of symptoms that can be a result of local or systemic infection. While localized damage does not usually result in extensive yield loss, systemic infection can have a severe impact on the productivity of crops grown for seed or floral parts.

Presently few agents are known which can be used to control white rust in radish. The control generally relies on a combination of management practices (controlled watering, ventilation, balanced program of nutrition) and a fungicide spray program. However, an increasing number of countries have a policy aimed at reducing the use of crop protection agents. If the use of control agents is no longer allowed at all, this can result in major problems in the cultivation of radish.

In vegetable crops the quality aspect is particularly important. Vegetables such as round red hybrids of radish infected by white blister are no longer sellable because of the cosmetic damage. There is therefore a great need for round red hybrids of radish which are resistant to white rust. Some resistances have been identified in radish germplasm, for example, see "Nature and Inheritance of Resistance to *Albugo candida* in radish", Williams and Pound, October 1963, *Phytopath*. Vol 53, but about 45 years later, there are still no round red radish hybrids or varieties resistant to *Albugo candida* that are commercially available.

Resistance to *Albugo candida* in round red radish would assist in the control of white rust. This would not only increase the stability of crop protection, it would also result in fewer environmentally harmful fungicide applications that are not always useful in controlling white rust.

The present invention, inbred radish line NIZ-AC2, is a round red radish line with resistance to white rust. In addition to the white rust resistance, NIZ-AC2 also has resistance to *Fusarium oxysporum*. The present invention is the first round red radish line with resistance to white rust (an oomycete) and to *Fusarium* (a fungus) known to the inventor. Radish inbred line NIZ-AC2 has high resistance against white blister (*Albugo candida*), resistance which is inherited in the hybrids produced with NIZ-AC2 as a parent. The highly resistant hybrids made with this line are the first *Albugo candida* highly resistant varieties in the round red radish market. Prior to the present invention, there were no round red radishes with resistance to white blister known to the inventor. In pathology tests, the resistance appears to be driven by a monogenic resistance gene that is readily transferred between the deposited cultivar and other red round radishes, including the hybrids and the three-way hybrids according to the present invention.

Radish inbred line NIZ-AC2 is an inbred line with very high yield potential in hybrids. Key factors in yield potential in radish are uniformity, earliness, cracking, leaf attachment and leaf health. An early radish variety is mainly very important in the winter growing season. In that period, cold weather can make a difference of 14 days in harvest between an early and a late variety (this difference is only 4 days in the summer period). Early harvest makes it possible to sow another crop or to sow radish again, this increases the return on investment per acre. Uniformity directly influences the number of radishes that can be sold per acre and reduces the labor costs because when radishes are bunched, all too-small radishes must be removed (extra labor). For the pre-pack market, all too-small radishes are thrown away which also means a loss. Cracking directly influences the return on investment. Radishes cracked during cultivation must be removed during bunching (which creates extra labor cost) and during processing in the pre-pack procedure. For the bunching market leaf health is a very important character. Leaves with disease damage are not attractive for consumers and have a bad shelf life. White blister on leaves make a bunch of radishes unattractive and because of dying of leaf tissue it results in an unsellable bunch. Leaf attachment directly influences the number of radishes harvested by machines or hand. Poor leaf attachment makes it very difficult to rapidly harvest radishes.

NIZ-AC2 has superior characteristics, and provides an excellent male line in crosses for producing first generation $F_1$ hybrid radish. Inbred radish line NIZ-AC2 is best adapted to the spring, winter and autumn growing seasons in the United States. Hybrids that are adapted to these maturity zones can be grown on a significant number of acres as it relates to the total of the USA radish acres. NIZ-AC2 produces an abundant volume of pollen for a long time which makes it an ideal pollinator i.e. useful as a male parent, for radish seed production. Inbred radish line NIZ-AC2 has very thick leaves which is a trait inherited in the $F_1$. This makes it very useful for handling bad weather conditions during cultivation (like rain and hail) and improves the shelf life of the bunched radishes. Inbred radish line NIZ-AC2 has very upright leaves which is a trait inherited in the $F_1$. This makes it very useful for mechanical harvesting, which is a key factor for pre-pack cultivation. This becomes more and more important in the bunching market with the introduction of the bunching machine. Inbred radish line NIZ-AC2 has an extremely thick skin, which makes it very useful for both pre-pack and bunching. This thick skin protects the radish against skin damage due to cleaning procedures which often result in radishes with white spots on the skin because skin is washed off in places. This is a major problem of many varieties mainly for the pre-pack market. The thick skin of the present invention combined with a nice white interior creates a very nice presentation when the radishes are sliced. Radish inbred line NIZ-AC2 and the hybrids made with this male line have tall tops which cover the soil in an early stage. This helps with weed control.

Radish inbred line NIZ-AC2 has many spines. One of the main problems with the mechanical harvesting of radishes is weak leaf attachment, which creates large losses in the number of harvested radishes. Radish inbred line NIZ-AC2 has a very thick leaf attachment, a trait which is also inherited in the $F_1$. This makes hybrids produced with NIZ-AC2 as a parent very suitable for mechanical harvesting.

Radish NIZ-AC2 has an excellent white interior (but some red coloration may develop under adverse conditions) with a high level of tolerance against pithiness even under cold weather conditions. The root of NIZ-AC2 is large with many secondary roots. Radish inbred line NIZ-AC2 is also tolerant against cracking under various growing conditions.

During the development of the inbred line NIZ-AC2 crosses were made to inbred testers for the purpose of estimating the line's general and specific combining ability and evaluations were run in Florida, Arizona, Michigan and Ohio. The inbred has proven to have a good combining ability in many hybrid combinations for earliness, uniformity, cracking and white blister resistance.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in NIZ-AC2.

Inbred radish line NIZ-AC2 has the following morphologic and other characters (based primarily on data collected at Florida, Arizona, Michigan, Ohio and greenhouse white blister trials).

TABLE 1

VARIETY DESCRIPTION INFORMATION

General Plant Information:

| | |
|---|---|
| Ploidy: | Diploid |
| Seedling - Anthocyanin coloration of hypocotyls: | Absent |
| Foliage - width of attachment: | Wide |
| Time of harvest maturity: | Late |

Leaf:

| | |
|---|---|
| Attitude: | Erect |
| Length: | Tall |

Blade:

| | |
|---|---|
| Shape: | Broad obovate |
| Intensity of green color: | Medium |
| Number of lobes: | Medium |
| Pubescence: | Strong |

Petiole:

| | |
|---|---|
| Anthocyanin coloration: | Absent |

Radish:

| | |
|---|---|
| Width of root: | Thick |
| Shape: | Circular |
| Shape of crown: | Convex |
| Shape of base: | Rounded |
| Coloration of skin: | Uniform |
| Color of upper part: | Red |
| Expression of red color of upper part: | Scarlet |
| Thickness of cortex: | Very thick |
| Color of flesh: | Opaque |
| Tendency to become pithy: | Absent or very weak |
| Resistance to pest and diseases: | Resistant to *Fusarium oxysporum* Resistant to *Albugo candida* |

Radish NIZ-AC2 is similar to the open-pollinated variety Red Silk, but there are numerous differences. Red Silk is susceptible to white blister (*Albugo candida*) while the present invention, the inbred line NIZ-AC2, is highly resistant to white blister. The leaves of the present invention, NIZ-AC2, are longer, more upright and thicker than the leaves of Red Silk. In addition, the skin of NIZ-AC2 is considerably thicker than Red Silk.

FURTHER EMBODIMENTS OF THE INVENTION

This invention is also directed to methods for producing a radish plant by crossing a first parent radish plant with a second parent radish plant wherein either the first or second parent radish plant is an inbred radish plant of the line NIZ-AC2. Further, both first and second parent radish plants can come from the inbred radish line NIZ-AC2. When self-pollinated, or crossed with another inbred line NIZ-AC2 plant, the inbred line NIZ-AC2 will be stable while when crossed with another, different radish line, an $F_1$ hybrid seed is produced. Said $F_1$ hybrid seed could be a three-way hybrid seed if the another, different radish is not a line, but a hybrid. For ease of understanding, an $F_1$ hybrid and a $F_1$ three-way hybrid are both called $F_1$ hybrids herein.

An inbred line has been produced through several cycles of self-pollination and is therefore to be considered as a homozygous line. An inbred line can also be produced though the dihaploid system which involves doubling the chromosomes from a haploid plant thus resulting in an inbred line that is genetically stable (homozygous) and can be reproduced without altering the inbred line. A hybrid variety is classically created through the fertilization of an ovule from an inbred parental line by the pollen of another, different inbred parental line. Due to the homozygous state of the inbred line, the produced gametes carry a copy of each parental chromosome. As both the ovule and the pollen bring a copy of the arrangement and organization of the genes present in the parental lines, the genome of each parental line is present in the resulting $F_1$ hybrid, theoretically in the arrangement and organization created by the plant breeder in the original parental line.

As long as the homozygosity of the parental lines is maintained, the resulting hybrid cross is stable. The $F_1$ hybrid is then a combination of phenotypic characteristics issued from two arrangement and organization of genes, both created by one skilled in the art through the breeding process.

Still further, this invention also is directed to methods for producing an inbred radish line NIZ-AC2-derived radish plant by crossing inbred radish line NIZ-AC2 with a second radish plant and growing the progeny seed, and repeating the crossing and growing steps with the inbred radish line NIZ-AC2-derived plant from 0 to 7 times. Thus, any such methods using the inbred radish line NIZ-AC2 are part of this invention: selfing, backcrosses, hybrid production, crosses to populations, and the like. All plants produced using inbred radish line NIZ-AC2 as a parent are within the scope of this invention, including plants derived from inbred radish line NIZ-AC2. Advantageously, the inbred radish line is used in crosses with other, different, radish inbreds to produce first generation ($F_1$) radish hybrid seeds and plants with superior characteristics.

It should be understood that the inbred can, through routine manipulation of cytoplasmic or other factors, be produced in a male-sterile form. Such embodiments are also contemplated within the scope of the present claims. As used herein, the term plant includes plant cells, plant protoplasts, plant cell tissue cultures from which radish plants can be regenerated, plant calli, plant clumps and plant cells that are intact in plants or parts of plants, such as embryos, pollen, ovules, flowers, seeds, roots, root tips, anthers, pistils, stem, meristematic cells and the like.

Duncan, et al. (*Planta,* 1985, 165:322-332) indicates that 97% of the plants cultured that produced callus were capable of plant regeneration. Subsequent experiments with both inbreds and hybrids produced 91% regenerable callus that produced plants. In a further study in 1988, Songstad, et al. (*Plant Cell Reports,* 7:262-265) reports several media additions that enhance regenerability of callus of two inbred lines. Other published reports also indicated that "nontraditional" tissues are capable of producing somatic embryogenesis and plant regeneration. K. V. Rao et al., (*Maize Genetics Cooperation Newsletter,* 1986, 60:64-65) refer to somatic embryogenesis from glume callus cultures and B. V. Conger, et al. (*Plant Cell Reports,* 1987, 6:345-347) indicate somatic embryogenesis from the tissue cultures of corn leaf segments. Thus, it is clear from the literature that the state of the art is such that these methods of obtaining plants are routinely used and have a very high rate of success.

When the term inbred radish plant is used in the context of the present invention, this also includes any inbred radish plant where one or more desired trait has been introduced through backcrossing methods. Backcrossing methods can be used with the present invention to improve or introduce one or more characteristic into the inbred. The term backcrossing as used herein refers to the repeated crossing of a hybrid progeny back to one of the parental radish plants for that inbred. The parental radish plant which contributes the gene or the genes for the desired characteristic is termed the nonrecurrent or donor parent. This terminology refers to the fact that the nonrecurrent parent is used one time in the backcross protocol and therefore does not recur. The parental radish plant to which the gene or genes from the nonrecurrent parent are transferred is known as the recurrent parent as it is used for several rounds in the backcrossing protocol (Fehr, 1987).

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a radish plant is obtained wherein all the desired morphological and physiological characteristics of the recurrent parent are recovered in the converted plant in addition to the gene or genes transferred from the nonrecurrent parent. It should be noted that some, one, two, three or more, self-pollination and growing of a population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving time, money and effort for the breeder. A non limiting example of such a protocol would be the following: a) the first generation $F_1$ produced by the cross of the recurrent parent A by the donor parent B is backcrossed to parent A, b) selection is practiced for the plants having the desired trait of parent B, c) selected plants are self-pollinated to produce a population of plants where selection is practiced for the plants having the desired trait of parent B and the physiological and morphological characteristics of parent A, d) the selected plants are backcrossed one, two, three, four, five or more times to parent A to produce selected backcross progeny plants comprising the desired trait of parent B and the physiological and morphological characteristics of parent A. Step c) may or may not be repeated and included between the backcrosses of step d.

The selection of a suitable recurrent parent is an important step for a successful backcrossing procedure. The goal of a backcross protocol is to alter or substitute one or more trait(s) or characteristic(s) in the original inbred. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass not only visual inspection and simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic, require selfing the progeny to determine which plant carry the recessive allele(s).

Many single gene traits have been identified that are not regularly selected for in the development of a new inbred but that can be improved by backcrossing techniques. Single gene traits may be naturally present in the non recurrent parent, examples of these traits include but are not limited to, male sterility, herbicide resistance, resistance for bacterial, fungal, or viral disease, insect resistance, male fertility, water stress tolerance, enhanced nutritional quality, increased digestibility, yield stability and yield enhancement.

In 1981, the backcross method of breeding accounted for 17% of the total breeding effort for inbred corn line development in the United States, according to, Hallauer, A. R. et al. (1988) "Corn Breeding" in *Corn and Corn Improvement*, No. 18, pp. 463-481. The backcross breeding method is similarly used for radish breeding and this method provides a precise way of improving varieties that excel in a large number of attributes but are deficient in a few characteristics. The method makes use of a series of backcrosses to the variety to be improved during which the character or the characters in which improvement is sought is maintained by selection. At the end of the backcrossing, the gene or genes being transferred unlike all other genes will be heterozygous. Selfing after the last backcross produces homozygosity for this gene pair(s) and, coupled with selection, will result in a variety with the adaptation, yielding ability and quality characteristics of the recurrent parent but superior to that parent in the particular characteristic(s) for which the improvement program was undertaken. Therefore, this method provides the plant breeder with a fairly high degree of genetic control of his work.

Backcrossing is a powerful mechanism for achieving homozygosity and any population obtained by backcrossing may rapidly converge on the genotype of the recurrent parent. When backcrossing is made the basis of a plant breeding program, the genotype of the recurrent parent will be modified with regards to genes being transferred, which are maintained in the population by selection.

Examples of successful backcrosses are the transfer of stem rust resistance from "Hope" wheat to "Bart" wheat and the transfer of bunt resistance to "Bart" wheat to create "Bart 38" which has resistance to both stem rust and bunt. Also highlighted by Allard (Allard, 1960, *Principles of Plant Breeding*, John Wiley & Sons, Inc.) is the successful transfer of mildew, leaf spot and wilt resistances in "California Common" alfalfa to create "Caliverde". The "Caliverde" variety produced through the backcross process is indistinguishable from "California Common" except for its resistance to the three named diseases.

One of the advantages of the backcross method is that the breeding program can be carried out in almost every environment that will allow the development of the character being transferred. Another advantage of the backcross method is that more than one character or trait can be transferred, either through several backcrosses or through the use of transformation and then backcrossing.

The backcross technique is not only desirable when breeding for disease resistance but also for the adjustment of morphological characters, color characteristics and simply inherited quantitative characters such as earliness, plant height and seed size and shape. In this regard, a medium grain type variety, "Calady", has been produced by Jones and Davis. In dealing with quantitative characteristics, they selected the donor parent with the view of sacrificing some of the intensity of the character for which it was chosen, i.e. grain size. "Lady Wright", a long grain variety was used as the donor parent and "Coloro", a short grain one as the recurrent parent. After four backcrosses, the medium grain type variety "Calady" was produced.

By means of the present invention, radish plants can be altered through genetic engineering or through traditional breeding practices to express various phenotypes of interest. Through the transformation of radish, expression of genes can be altered or DNA sequences can be inserted. DNA sequences native to radish as well as non-native DNA sequences can be transformed or bred into radish and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Genes can be altered or inserted into radish plants to produce radish plants with certain desired traits such as male sterility, male fertility, herbicide resistance, insect resistance, disease resistance, water stress tolerance, and increased digestibility. For examples of genes, promoters etc. which alter male sterility, see international publications WO 01/29237, WO 92/13956 and WO 92/13957, publication Paul et al., *Plant Mol. Biol.* 19:611-622, 1992), and U.S. Pat. Nos. 5,859,341, 6,297,426, 5,478,369; 5,824,524, 5,850,014 and 6,265,640.

For examples of genes, promoters etc. which provide or alter herbicide resistance, see Lee et al., *EMBO J.* 7:1241 (1988) and Miki et al., *Theor. Appl. Genet.* 80:449 (1990); U.S. Pat. No. 4,940,835 to Shah, et al., which discloses the nucleotide sequence of a form of EPSPS which can confer glyphosate resistance; U.S. Pat. No. 5,627,061 to Barry et al. also describes genes encoding EPSPS enzymes; U.S. Pat. Nos. 6,566,587; 6,338,961 6,248,876, 6,040,497, 5,804,425, 5,633,435, 5,145,783, 4,971,908, 5,312,910, 5,188,642, 4,940,835, 5,866,775, 6,225,114, 6,130,366, 5,310,667, 4,535,060, 4,769,061, 5,633,448, 5,510,471, RE 36,449, RE 37,287 E, and 5,491,288; international publications EP1173580, WO 01/66704, EP1173581 and EP1173582; U.S. Pat. Nos. 5,776,760 and 5,463,175, U.S. application Ser. No. 10/427,692, U.S. Pat. Nos. 4,769,061 and 4,975,374; European Application No. 0 242 246; Marshall et al., *Theor. Appl. Genet.* 83:435 (1992); U.S. Pat. No. 4,810,648; Hayes et al., *Biochem. J.* 285:173 (1992), Hattori et al., *Mol. Gen. Genet.* 246:419, (1995), U.S. Pat. Nos. 6,288,306, 6,282,837, 5,767,373, and international publication WO 01/12825.

For examples of insect resistance genes, promoters, etc. that can be introduced or altered to provide insect resistance in radish, see PCT Application WO 96/30517, PCT Application WO 93/19181; Geiser et al., *Gene* 48:109 (1986); PCT Application US 93/06487; Hammock et al., *Nature* 344:458 (1990), Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin identified in *Diploptera puntata*); Chattopadhyay et al. (2004) *Critical Reviews in Microbiology* 30 (1): 33-54 (2004); Zjawiony (2004) *J Nat Prod* 67 (2): 300-310; Carlini & Grossi-de-Sa (2002) *Toxicon*, 40 (11):1515-1539; Ussuf et al. (2001) *Curr Sci.* 80(7):847-853; and Vasconcelos & Oliveira (2004) *Toxicon* 44 (4):385-403; U.S. Pat. No. 5,266,317 to Tomalski et al., which discloses genes encoding insect-specific paralytic neurotoxins; Taylor et al., Abstract #497, Seventh Int'l Symposium on Molecular Plant-Microbe Interactions (Edinburgh, Scotland) (1994) (insect-specific antibody or an immunotoxin).

For examples of disease resistance genes, promoters, etc. that can be introduced or altered to provide disease resistance in radish, see Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (Arabidopsis RSP2 gene for resistance to *Pseudomonas syringae*), McDowell & Woffenden, (2003) *Trends Biotechnol.* 21(4): 178-83 and Toyoda et al., (2002) *Transgenic Res.* 11 (6):567-82; Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I); Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996); PCT Application WO 93/02197 (Scott et al.), *Plant Molec. Biol.* 21:673 (1993) (nucleotide sequence of the parsley ubi4-2 polyubiquitin gene); U.S. Pat. Nos. 7,145,060, 7,087,810 and 6,563,020; Botella et al., *Plant Molec. Biol.* 24:757 (1994), (nucleotide sequences for mung bean calmodulin cDNA clones) and Griess et al., *Plant Physiol.* 104:1467 (1994) (nucleotide sequence of a maize calmodulin cDNA clone); PCT Application WO 95/16776 and U.S. Pat. No. 5,580,852, which disclose peptide derivatives of tachyplesin which inhibit fungal plant pathogens, and PCT Application WO 95/18855 and U.S. Pat. No. 5,607,914 which teaches synthetic antimicrobial peptides that confer disease resistance; Briggs, S., *Current Biology*, 5(2) (1995); Pieterse & Van Loon (2004) *Curr. Opin. Plant Bio.* 7(4):456-64 and Somssich (2003) *Cell* 113 (7):815-6 (systemic acquired resistance); Cornelissen and Melchers, *Plant Physiol.*, 101:709-712 (1993); Parijs et al., *Planta* 183:258-264 (1991) and Bushnell et al., *Can. J. of Plant Path.* 20(2):137-149 (1998), U.S. Pat. No. 6,875,907 (antifungal genes); U.S. Pat. No. 5,792,931; U.S. Pat. No. 7,205,453 (cystatin and cysteine proteinase inhibitors); WO 03/000863 and U.S. Pat. No. 6,911,577 (defensin genes).

For examples of genes, promoters, etc. conferring water stress tolerance and/or tolerance to other types of abiotic stress, see WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, and 6,801,104; international patent applications WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521, and WO 99/38977; US 2004/0148654 and WO 01/36596 where abscisic acid is altered in plants resulting in improved plant phenotype such as increased yield and/or increased tolerance to abiotic stress; WO 2000/006341, WO 04/090143, U.S. application Ser. No. 10/817,483 and U.S. Pat. No. 6,992,237 where cytokinin expression is modified resulting in plants with increased stress tolerance, such as drought tolerance, and/or increased yield; U.S. Pub. No. 20040098764 or U.S. Pub. No. 20040078852 (plant transcription factors or transcriptional regulators of abiotic stress).

TABLES OF FIELD TEST TRIALS

In the tables that follow, the traits and characteristics of hybrid combinations having radish inbred line NIZ-AC2 as a parental line are given compared to other hybrids. The hybrid combinations having radish inbred line NIZ-AC2 as a parental line are three-way hybrids, meaning the NIZ-AC2 inbred line has been crossed with a hybrid. The data collected are presented for key characteristics and traits. The field tests are experimental trials and have been made at numerous locations. Concerning white blister (*Albugo candida*), the disease was present in Florida two years in a row but not present in Arizona. Information about these experimental hybrids and the inbred line NIZ-AC2 in open field trials compared to the check hybrids is presented in Tables 2 to 4. Information about phytopathology tests on *Albugo candida* and *Fusarium oxysporum* is presented in Table 5.

Table 2 shows a comparison between the present invention radish inbred line NIZ-AC2, hybrids resulting from crosses between NIZ-AC2 as the male parent and radish hybrids, and commercial radish hybrids for several characteristics. In Table 2, column 1 shows the inbred or hybrid, column 2 shows the reaction to white blister (*Albugo candida*), column 3 shows the score for earliness, column 4 shows the score for pithiness, column 5 shows the score for color thickness, column 6 shows the erectness of the leaves, column 7 shows the score for leaf thickness and column 8 shows the score for leaf attachment. The scores are based on a visual scale of 1 to 9 where 1 is poor and 9 is excellent. The data in Table 2 were collected in the Belle Glade area of Florida in 2009.

Table 3 shows a comparison between radish hybrids produced using the present invention, radish inbred line NIZ-AC2 as the male parent, with a radish inbred (Red Silk) and commercial radish hybrids for their reactions to white blister (*Albugo candida*). The data were collected in 2008 in the Belle Glade area of Florida. Column 1 shows the inbred or hybrid and column 2 show the white blister reaction where HR means high resistance.

TABLE 3

Comparison between radish hybrids produced with NIZ-AC2 as the male parent, a radish inbred and commercial radish hybrids.

| Name variety/inbred line | *Albugo candida* on leaves |
|---|---|
| Red Silk | Susceptible |
| Hybrids with male line NIZ-AC2 | |
| NIZ 34-115 F1 | HR (100%) |
| NIZ 34-116 F1 | HR (100%) |
| NIZ 34-117 F1 | HR (100%) |
| Commercial hybrids | |
| Red Satin F1 | Susceptible |
| Agora F1 | Susceptible |
| Crunchy Red F1 | Susceptible |

Table 4 shows a comparison between radish hybrids produced using the present invention, radish inbred line NIZ-AC2 as the male parent, with a radish inbred (Red Silk) and commercial radish hybrids for various traits. The data were collected in 2009 in the Phoenix area of Arizona. Each trait was evaluated and scored. The scores are based on a visual scale of 1 to 9 where 1 is poor and 9 is excellent. Column 1 shows the variety or hybrid, column 2 shows the earliness score, column 3 shows the pithiness score, column 4 shows the color thickness and column 5 shows the erectness of the leaves.

TABLE 2

Comparison of various traits between radish inbred line NIZ-AC2, radish hybrids made with NIZ-AC2 and commercial radish hybrids.
Florida April 2009
Belle Glade area

| Name variety/inbred line | Traits | | | | | | |
|---|---|---|---|---|---|---|---|
| | *Albugo Candida* on leaves | Earliness | Pithiness | Color Thickness | Erect Leaves | Leaf Thickness | Leaf Attachment |
| NIZ-AC2 | HR (100%) | | 9 | 9 | 8 | 9 | 9 |
| Red Silk | Susceptible | | 9 | 7 | Medium-erect | 8 | 7 |
| Hybrids with male line NIZ-AC2 | | | | | | | |
| NIZ 34-115 F1 | HR (100%) | 9 | 8 | 8 | Very erect | 9 | 8 |
| NIZ 34-116 F1 | HR (100%) | 8 | 8 | 8 | Very erect | 9 | 8 |
| NIZ 34-117 F1 | HR (100%) | 8 | 8 | 8 | Very erect | 9 | 8 |
| Commercial hybrids | | | | | | | |
| Red Satin F1 | Susceptible | 7 | 6 | 5 | Medium erect | 6 | 6 |
| Agora F1 | Susceptible | 7 | 6 | 4 | Medium erect | 6 | 6 |
| Crunchy Royale F1 | Susceptible | 7 | 5 | 6 | Not erect | 8 | 6 |
| Crunchy Red F1 | Susceptible | 5 | 5 | 6 | Not erect | 8 | 6 |

HR = High resistance

TABLE 4

Comparison of various traits between radish hybrids made with NIZ-AC2, a commercial radish inbred and commercial radish hybrids.
Arizona 2009
Phoenix area

| Name variety/inbred line | Earliness | Pithiness | Color Thickness | Erect Leaves |
|---|---|---|---|---|
| Red Silk | 3 | 7 | 7 | Medium-erect |
| Hybrids with male line NIZ-AC2 | | | | |
| NIZ 34-115 F1 | 8 | 9 | 8 | Very erect |
| NIZ 34-116 F1 | 8 | 8 | 8 | Very erect |
| NIZ 34-117 F1 | 8 | 8 | 8 | Very erect |
| Commerical hybrids | | | | |
| Red Satin F1 | 6 | 7 | 6 | Medium-erect |
| Agora F1 | 7 | 6 | 6 | Medium-erect |
| Crunchy Royale F1 | 8 | 6 | 6 | Not erect |
| Crunchy Red F1 | 5 | 6 | 5 | Not erect |

Table 5A shows a comparison of the reactions to white blister (*Albugo candida*) between the present invention, radish inbred line NIZ-AC2, three susceptible checks and three radish hybrids produced by using NIZ-AC2 as the male parent. Table 5B shows a comparison of the reactions to *Fusarium oxysporum* between the present invention, radish inbred line NIZ-AC2 and a commercial susceptible check. The data were collected in 2009 in a greenhouse. HR means high resistance. Column 1 shows the variety or hybrid, column 2 shows the disease reaction to white blister on the radish cotyledons and column 3 shows the disease reaction to white blister on the radish leaves.

TABLE 5A

*Albugo candida*

| Variety/line | *Albugo* on cotyledons | *Albugo* on leaves |
|---|---|---|
| NIZ-AC2 | HR (100%) | HR (100%) |
| Susceptible check | Susceptible | Susceptible |
| NIZ-AC2 | HR (100%) | HR (100%) |
| Susceptible check | Susceptible | Susceptible |
| NIZ-AC2 | HR (>95%) | HR (>95%) |
| Susceptible check | Susceptible (<15%) | Susceptible (<15%) |
| NIZ 34-115 | HR (>90%) | HR (>90%) |
| NIZ 34-116 | HR (>94%) | HR (>95%) |
| NIZ 34-117 | HR (100%) | HR (100%) |

TABLE 5B

*Fusarium oxysporum*

| Variety/line | *Fusarium* on cotyledons |
|---|---|
| NIZ-AC2 | HR (96%) |
| Marabelle | Susceptible |
| NIZ-AC2 | HR (100%) |
| Marabelle | Susceptible |

DEPOSIT INFORMATION

A deposit of the Nickerson Zwaan B. V. proprietary Inbred Radish line NIZ-AC2 disclosed above and recited in the appended claims has been made with the National Collections of Industrial, Food and Marine Bacteria (NCIMB), 23 St Machar Drive, Aberdeen, Scotland, AB24 3RY, United Kingdom. The date of deposit was Aug. 16, 2010. The deposit of 2,500 seeds was taken from the same deposit maintained by Nickerson Zwaan B. V. since prior to the filing date of this application. All restrictions will be removed upon granting of a patent, and the deposit is intended to meet all of the requirements of 37 C.F.R. §§1.801-1.809. The NCIMB Accession number is 41753. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A seed of radish inbred line designated NIZ-AC2, wherein a representative sample of seed of said line was deposited under NCIMB Accession No. 41753.

2. A radish plant, or a part thereof, produced by growing the seed of claim 1.

3. A radish plant or a part thereof, having all the physiological and morphological characteristics of the inbred line NIZ-AC2, wherein a representative sample of seed of said line was deposited under NCIMB Accession No. 41753.

4. A tissue culture of cells produced from the plant of claim 2, wherein said cells of the tissue culture are produced from a plant part selected from the group consisting of leaf, pollen, ovule, embryo, root, root tip, anther, pistil, flower, cotyledon, hypocotyl, meristematic cell, seed, shoot, stem and petiole.

5. A radish plant regenerated from the tissue culture of claim 4, wherein the regenerated plant has all the morphological and physiological characteristics of inbred line NIZ-AC2, wherein a representative sample of seed of said line was deposited under NCIMB Accession No. 41753.

6. A method for producing a hybrid radish seed, wherein the method comprises crossing the plant of claim 2 with a different radish plant and harvesting the resultant hybrid radish seed.

7. A hybrid radish seed produced by the method of claim 6.

8. A hybrid plant produced by the hybrid radish seed of claim 7.

9. The method of claim 6 wherein the different radish plant is a hybrid radish plant.

10. A hybrid radish seed produced by the method of claim 9 wherein the hybrid radish seed is a three-way hybrid seed.

11. A hybrid plant produced by the hybrid radish seed of claim 10.

12. A method for producing inbred line NIZ-AC2, wherein a representative sample of seed of said line was deposited under NCIMB Accession No. 41753, wherein the method comprises:
   a) planting a collection of seed comprising seed of a hybrid, one of whose parents is inbred line NIZ-AC2, said collection also comprising seed of said inbred;

b) growing plants from said collection of seed;
c) identifying the plants having the physiological and morphological characteristics of radish inbred line NIZ-AC2 as inbred parent plants;
d) controlling pollination of said inbred parent plants in a manner which preserves the homozygosity of said inbred parent plant; and
e) harvesting the resultant seed.

13. A method of introducing a desired trait into radish inbred line NIZ-AC2, wherein the method comprises:
a) crossing the inbred line NIZ-AC2 plants grown from the inbred line NIZ-AC2 seed, wherein a representative sample of seed of said line was deposited under NCIMB Accession No. 41753, with plants of another radish line that comprise a desired trait to produce progeny plants, wherein the desired trait is selected from the group consisting of male sterility, male fertility, herbicide resistance, insect resistance, disease resistance, water stress tolerance, and increased digestibility;
b) selecting progeny plants that have the desired trait to produce selected progeny plants;
c) crossing the selected progeny plants with the inbred line NIZ-AC2 plants to produce backcross progeny plants;
d) selecting for backcross progeny plants that have the desired trait and physiological and morphological characteristics of radish inbred line NIZ-AC2 listed in Table 1 to produce selected backcross progeny plants; and
e) repeating steps (c) and (d) one or more times in succession to produce selected second or higher backcross progeny plants that comprise the desired trait and the physiological and morphological characteristics of radish inbred line NIZ-AC2 as listed in Table 1.

14. A radish plant produced by the method of claim 13, wherein the plant has the desired trait and all of the physiological and morphological characteristics of radish inbred line NIZ-AC2 as listed in Table 1.

15. A method for producing inbred line NIZ-AC2 seed, wherein a representative sample of seed of said line was deposited under NCIMB Accession No. 41753, wherein the method comprises crossing a first inbred parent radish plant with a second inbred parent radish plant and harvesting the resultant radish seed, wherein both said first and second inbred radish plant are the radish plant of claim 2.

16. A method for producing inbred line NIZ-AC2 seed, wherein a representative sample of seed of said line was deposited under NCIMB Accession No. 41753, wherein the method comprises:
a) planting an inbred radish seed of claim 1;
b) growing a plant from said seed;
c) controlling pollination in a manner that the pollen produced by the grown plant pollinates the ovules produced by the grown plant; and
d) harvesting the resultant seed.

17. A method for breeding *Albugo candida* resistant radish plant comprising crossing a radish plant selected from the group of plants of claim 2, of claim 8 or of claim 11, with another radish plant.

18. A round red radish seed having an *Albugo candida* resistance gene wherein a representative sample of seed containing said resistance gene has been deposited under NCIMB Accession No. 41753.

19. A round red radish seed having an *Albugo candida* resistance gene and having a *Fusarium oxysporum* resistance gene wherein a representative sample of seed containing said resistance gene has been deposited under NCIMB Accession No. 41753.

* * * * *